United States Patent [19]

Bocquet et al.

[11] Patent Number: 5,156,143

[45] Date of Patent: Oct. 20, 1992

[54] ULTRASONIC PERCUSSION DEVICE

[75] Inventors: Michel Bocquet, Issy les Moulineaux; Gérard Drobinski, Fontenay aux Roses; Daniel Kremer, Combes la Ville, all of France

[73] Assignee: Societe Anonyme dite: Aerospatiale Societe Nationale Industrielle, Paris, France

[21] Appl. No.: 599,627

[22] Filed: Oct. 18, 1990

[30] Foreign Application Priority Data

Oct. 18, 1989 [FR] France ................. 89 13618

[51] Int. Cl.$^5$ .............................. A61H 1/00
[52] U.S. Cl. ................... 128/24 AA; 178/661.03; 604/22; 606/128; 606/169
[58] Field of Search ........ 128/24 AA, 662.06, 662.03; 604/22, 43, 35; 606/169, 170, 171, 128; 433/86

[56] References Cited

U.S. PATENT DOCUMENTS

| | | |
|---|---|---|
| 2,071,954 | 2/1937 | Scruggs. |
| 3,990,452 | 11/1976 | Murry et al.. |
| 4,330,278 | 5/1982 | Martin ..................... 128/24 AA |
| 4,561,438 | 12/1985 | Bonnet et al. ............. 606/128 |
| 4,854,325 | 8/1989 | Stevens. |
| 4,867,141 | 9/1989 | Nakado ..................... 128/24 AA |
| 4,988,334 | 1/1991 | Hornlein ..................... 606/169 |

FOREIGN PATENT DOCUMENTS

WO89/06515 7/1989 PCT Int'l Appl..

Primary Examiner—Francis Jaworski
Assistant Examiner—Scott R. Akers
Attorney, Agent, or Firm—Marshall, O'Toole, Gerstein, Murray & Bicknell

[57] ABSTRACT

An ultrasonic percussion device uses an ultrasonic generator attached to one end of a wire by a linking assembly which includes a radially elastically deformable sleeve (7) receiving the end of the wire and provided with a conical flared section (7B); a hole (8) provided in a member (9) integral with the generator and into which the sleeve is able to be introduced, the conical section (7B) of the sleeve (7) coming into contact with a complementary conical wall (8B) provided in the hole, and a clamping element (10) able to cooperate by screwing with the member (9) and to act against the sleeve (7); the device is particularly useful for destroying atheromata in clogged arteries.

10 Claims, 3 Drawing Sheets

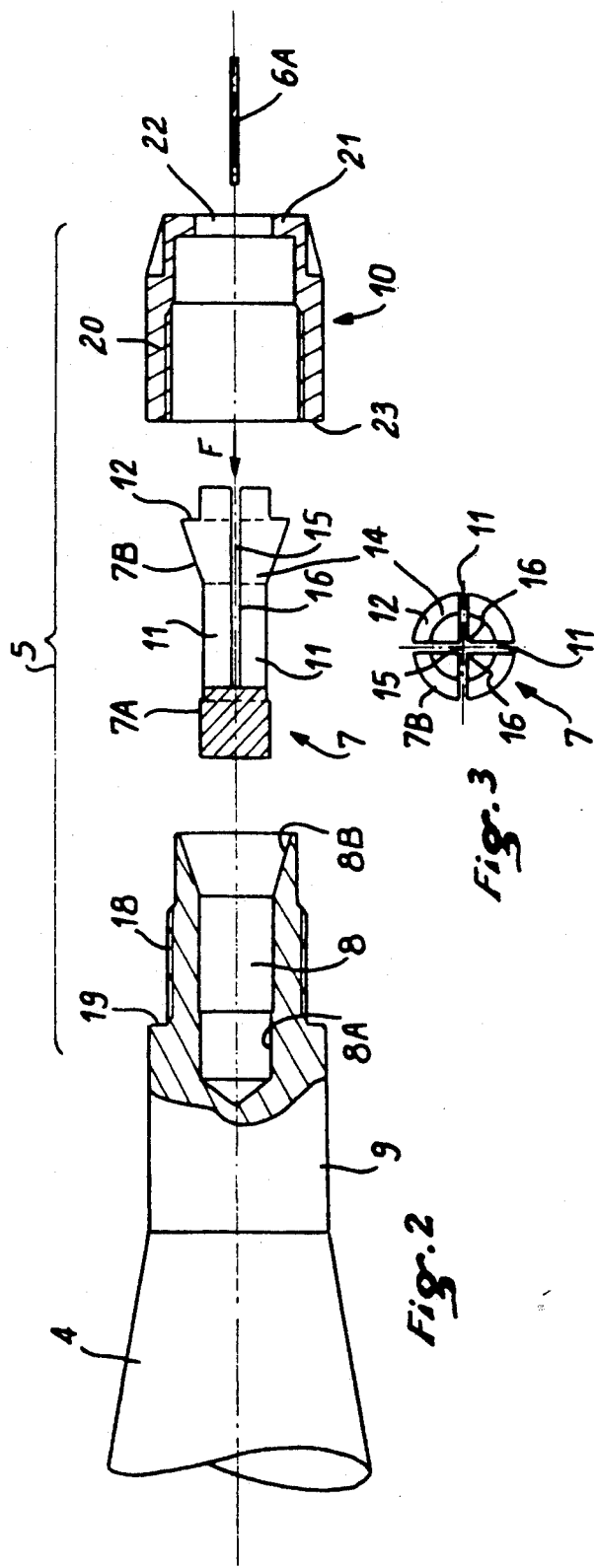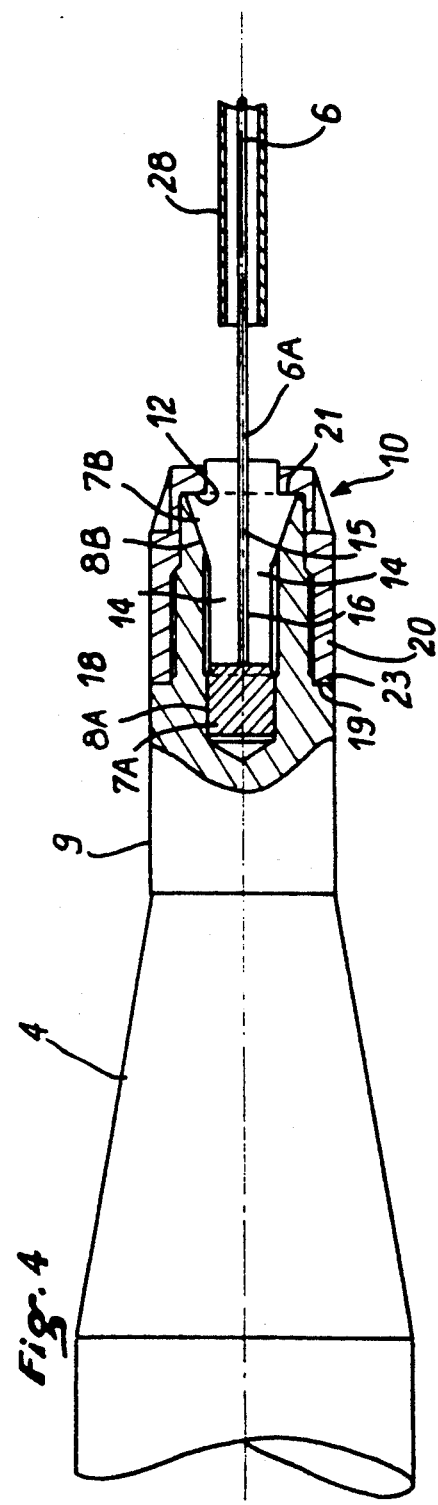

ULTRASONIC PERCUSSION DEVICE

FIELD OF THE INVENTION

The present invention concerns an ultrasonic percussion device.

BACKGROUND OF THE INVENTION

Although such a percussion device may be used for a large number of applications, such as machining, polishing, unclogging of pipes, etc., it shall be more particularly described hereafter as regards its medical usage. However, it goes without saying that this does not imply that the present invention is restricted to medical applications. As regards its medical application, the device of the invention is intended for the treatment of physical or morphological ducts, especially for the destruction of degenerated atheromata inside arteries.

In order to destroy atheromata, apart from using laser or rotary cutting tool devices, practitioners may use ultrasonic devices. These ultrasonic devices mainly include an ultrasonic generator to which the proximal end of a wire is connected by linking means, whereas the distal end of said wire is introduced by the practitioner into the physical duct to be treated until it comes into contact with the atheromata to be broken. The destruction of these is effected by means of the vibrations generated by the generator and transmitted to the wire whose distal end cyclically hammers the atheromata.

In reality, these ultrasonic devices, although based on a widely tested and technically controlled principle and do give encouraging results, do nevertheless have a certain number of drawbacks, in particular as regards the link between the proximal end of the wire and the ultrasonic generator.

In fact, the fixing of the proximal end of the wire to the ultrasonic generator needs to be such that the vibrations generated by the generator are transmitted integrally to the wire so as to obtain an optimal result. Now, it has been established that the linking means currently employed, owing in particular to the millimetric diameter of the wire and the inevitable operational plays occurring during vibrations, do not make it possible to ensure maximum transmission of the ultrasonic vibrations.

As a result, the energy of the vibrations of the wire s reduced and does not rapidly and effectively destroy the atheromata. In order to mitigate this loss of energy, practitioners are tending to increase the energy of the vibrations delivered by the generator, but then the calorific energy produced and released at the generator/wire link is such that it usually causes rupture of the wire.

In addition, the link between the proximal end of the wire and the generator may be embodied by means of a weld. However, in this case, the mechanical and thermic stresses produced render the wire extremely brittle and often result in it breaking. Furthermore, such an embodiment of the linking means no longer allows the wire to be dismantled.

SUMMARY OF THE INVENTION

The object of the present invention is to overcome these drawbacks and concerns an ultrasonic percussion device intended, for example, to destroy atheromata in arteries, wherein the conception of the wire/generator linking means is such that it makes it possible to totally in full safety transmit the vibrations generated by the generator to said wire, whilst also enabling the wire to be dismantled.

To this effect, the ultrasonic percussion device of the invention, said device comprising an ultrasonic generator and a wire whose proximal end is connected to said generator by linking means so that the distal end of said wire is driven by a percussion movement, is notable in that said linking means include:

- a sleeve radially elastically deformable receiving the proximal end of said wire and provided with a conical flared section;
- a hole provided in a member integral with said generator and into which said sleeve is able to be introduced, the conical section of said sleeve coming into contact with a complementary conical wall provided in said hole, and
- a clamping element able to cooperate by screwing with said member and act against said sleeve so that, at the time of screwing, the conical section of said sleeve is pressed against the complementary conical wall of said hole thus causing, b means of the radial deformation of said sleeve, the clamping of the proximal end of said wire until said clamping element comes into contact with a stop provided on said member.

Thus, according to the invention, the ultrasonic vibrations generated by the ultrasonic generator are transmitted optimally to said wire by means of the conical link between the member integral with the generator and the sleeve clamping the proximal end of the wire, said conical link being obtained by means of the clamping element which, by deforming it radially, presses the conical section of the sleeve against the corresponding section of said hole and which abuts against said member, thus creating an additional link.

Furthermore, it shall be observed that the wire may be easily dismantable by simply unscrewing the clamping element, the elastically radially deformable sleeve resuming its initial position. When the practitioner has destroyed an accumulation of matter contained in a physical duct with the aid of the ultrasonic vibrations transmitted by the wire, it is then possible to remove this duct a catheter, for example, whose distal end comprises a deformable ballonet. In this way, the practitioner may treat the portion of said duct which previously contained the accumulation of matter by deforming this portion, such a ballonet catheter not being able to be used previously since the duct portion to be treated was clogged up by the accumulation of matter to be destroyed.

In one preferred embodiment, said sleeve comprises a circular cylindrical section prolonged by said conical flared section, said cylindrical section being able to cooperate with the wall of said hole provided in said member, whereas the conical flared section of said sleeve abuts against the complementary conical wall of said hole.

Thus, the cylindrical section ensures the correct positioning of the sleeve with respect to the member integral with the ultrasonic generator, whereas the conical flared section allows for clamping of the proximal end of the wire.

So as to allow for the elastically radial deformation of said sleeve, radial slots are provided in at least the conical flared section of said sleeve. Advantageously, four radial slots are provided in said sleeve by being equiangularly distributed from one another. Thus, the conical flared section of said sleeve is approximately formed by four cone quarters whose internal edges parallel to the longitudinal direction of said sleeve abut against the proximal end of the wire by clamping it firmly.

In addition, said clamping element may include one threaded cylindrical lateral wall ended by an open bottom coming into contact with the end face of the flared section of said sleeve thus authorizing the passage of said wire, whereas the end face of said cylindrical lateral wall of said clamping element opposite said open bottom abuts against the stop of said member.

According to a further characteristic of the invention, the diameter of the wire is between 0.15 mm and 0.50 mm. Advantageously, the diameter of the wire is approximately equal to 0.4 mm. Thus, the clamping of the proximal end of the wire is effected in satisfactory conditions so as to enable the internal edges of the four cone quarter forming the conical flared section of the sleeve to firmly squeeze said proximal end of the wire.

In one preferred embodiment, the distal end of said wire is flattened. Advantageously, the distal end of said wire has an oblong section with one of its dimensions corresponding to the diameter of the wire, whereas the other dimension is smaller than said diameter. In this way, the distal end of the wire exhibits a certain flexibility in the direction corresponding to one with a smaller dimension. The practitioner may then suitably direct the distal end of the wire so as to facilitate the progression of the wire into the sinuosities of the physical duct.

In addition, so as to enable the practitioner to follow up on a display screen the advance of the wire in the physical duct to be treated and to control the effectiveness of the subsequent treatment by the ensuing ultrasounds, the wire is advantageously made of a radio-opaque material.

BRIEF DESCRIPTION OF THE DRAWINGS

The figures of the accompanying drawing shall clearly show how the invention may be embodied. Identical references on these figures denote similar elements.

FIG. 2 is a sectional exploded view of the linking means before being assembled for connecting the proximal end of the wire to the ultrasonic generator.

FIG. 3 is a view of the radially deformable sleeve along the arrow F of FIG. 2.

FIG. 4 is a sectional view of the linking means after being assembled connecting the proximal end of the wire to the ultrasonic generator.

DETAILED DESCRIPTION OF THE PREFERRED EMBODIMENTS

Figure 1:
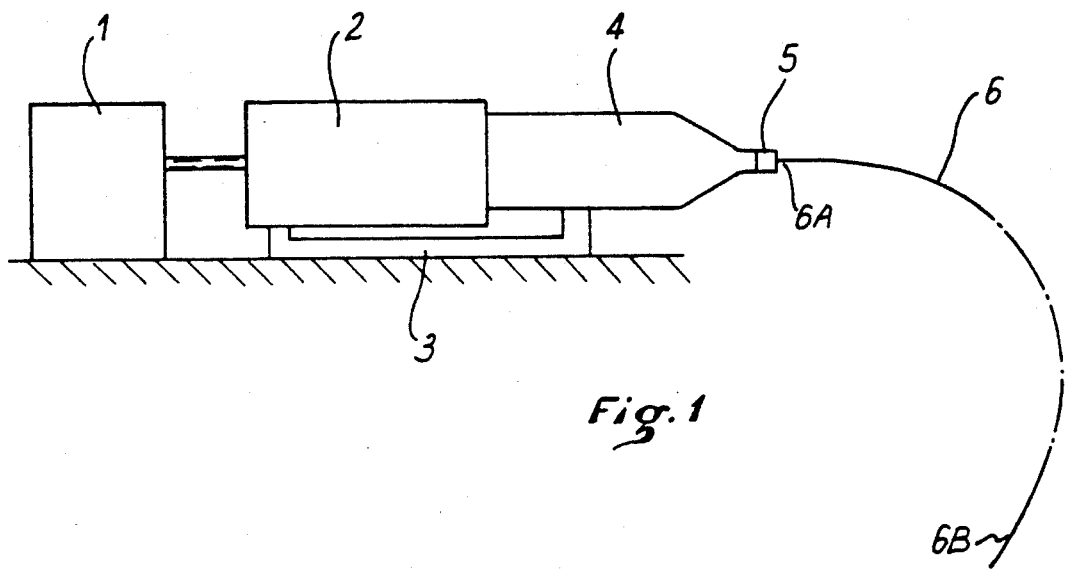
FIG. 1 diagrammatically represents in perspective an embodiment of the ultrasonic percussion device of the invention.

With reference to FIG. 1, the ultrasonic percussion device comprises a known type of an ultrasonic wave generator 1 connected to a piezoelectric transducer 2 mounted on a support 3. The transducer 2 receives, by means of transmission means 4 provided with linking means 5, the proximal end 6A of a wire 6 whose distal end 6B is able to be introduced into a physical duct to be treated so as to come into contact with certain obstacles, such as accumulations of matter resulting in the formation of atheromata inside the arteries, in order to destroy said obstacles. The destruction of athermoatic formation is obtained from the ultrasonic generator and the transducer 2 which converts the electric energy produced by the ultrasonic generator into mechanical energy transmitted in the form of mechanical vibrations along the wire, the distal end of the wire then cyclically hammering the obstructive atheromatic formation.

So that the mechanical energy generated by the transducer is fully transmitted to the wire, the linking means connecting the proximal end 6A of the wire to the transducer 2 include according to the invention an elastically radially deformable sleeve 7, a hole 8 provided in a revolution member 9 integral with the transmission means 4, and a clamping element 10.

With reference to FIG. 2, which shows the linking means 5 prior to being assembled, the sleeve 7, intended to receive the proximal end 6A of the wire, mainly comprises a circular cylindrical section 7A extended by a conical flared section 7B. In addition, radial slots 11 are provided in the sleeve 7 and in this embodiment extend from the end face 12 of the conical flared section 7B as far as into the circular section 7A.

FIG. 3 shows four radial slots 11 provided in the sleeve by being distributed equiangularly from one other and, at the location where these slots are made, thus delimiting four identical approximately frustoconical portions 14. Two opposing slots are thus found in with one in prolongation of the other in a common diametrical plane longitudinal to said sleeve. Owing to the presence of these slots 11, the sleeve 7 may be radially elastically deformable.

The proximal end 6A of the wire is able to be introduced into the axial passage 15 delimited by the internal edges 16 of the four portions 14 so as to be firmly maintained there by the latter.

FIG. 2 shows that the hole 8, made in the member 9 integral with the transducer 2, has at its opening end a conical wall 8B extending the cylindrical wall 8A of said hole. Thus, the cylindrical section 7A of the sleeve is able to cooperate with the cylindrical wall 8A of the hole 8, whereas the flared section 7B of the sleeve is able to cooperate with the complementary conical wall 8B of said hole.

In addition, a threading 18 is provided on the member 9 concentric to the hole 8 and ended by a radial annular shoulder 19 forming a stop.

The clamping element 10 includes a threaded cylindrical lateral wall 20 intended to cooperate with the threading 18 provided on the member 9 and ended by a bottom 21 provided with an opening 22 allowing for the passage of the proximal end 6A of the wire 6.

The end face 23 of the lateral wall 20 of the clamping element opposite the bottom 22 is intended to abut against the annular shoulder 19 provided on the member 9.

FIG. 4 shows the assembling of the linking means 5 allowing for the clamping of the proximal end 6A of the wire 6 and the transmission of the generated vibrations.

This figure shows that the sleeve 7 is introduced into the hole 8 of the member 9 integral with the transducer 2 so that its cylindrical section 7A cooperates via an adjustment with the corresponding cylindrical section 8A of the hole 8, which thus ensures a suitable positioning and centering of the sleeve 7 with respect to the hole 8 of the member 9.

The sleeve 7 is introduced until its conical flared section 7B comes into contact with the conical section 8B of said hole.

The proximal end 6A is engaged in the axial passage 15 of the sleeve 7 until it abuts against the bottom of the radial slots 11, the internal edges 16 of the portions 14 being flush with the proximal end 6A of the wire.

The clamping element 10, via the bottom 21 of which the wire 6 passes, is then screwed by its threaded lateral wall 20 to the threading 18 provided on the member 9.

At the time of screwing, the open bottom 21 of the element 10 abuts against the end face 12 of the conical section 7B of the sleeve thus pressing said conical section against the complementary conical wall 8B of the hole 8. By means of the radial slots 1, this results in the radial deformation of the portions 14 of the sleeve 7 which are strongly applied against the conical wall 8B and, at the same time, in the clamping of the proximal end 6A of the wire by the internal edges 16 of said portions. The clamping element 10 is screwed until it abuts with its end face 23 against the radial annular shoulder 19 of the member 9.

Thus, with these linking means 5, it is possible to readily understand that the vibrations generated by the ultrasonic generator and reproduced by the member 9 linked to the transducer 2 are optimally transmitted to the wire 6.

Figure 5:
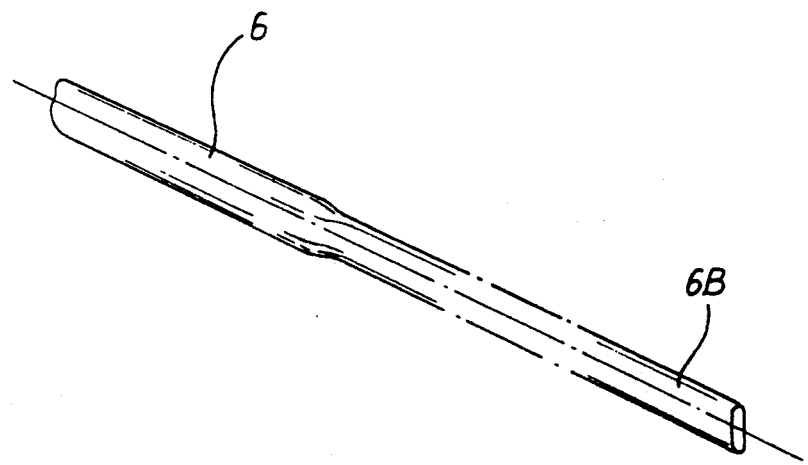
FIG. 5 shows in perspective one preferred embodiment of the distal end of said wire.

Furthermore, the distal end 6B of the latter is flattened, as shown on FIG. 5. This end 6B advantageously has one oblong section with one of its dimensions corresponding to the diameter of the wire, whereas the other dimension perpendicular to the preceding dimension is clearly smaller than the diameter of the wire. By virtue of the flexibility of the distal end 6B of the wire in the smaller direction, the practitioner is able to maximize orientation of the distal end of the wire so as to follow the sinuosities of the physical duct to be treated.

The wire is preferably made of a radio-opaque material enabling the practitioner to follow the position of the wire in the physical duct and monitor the effectiveness of the actual treatment. The diameter of the wire may be about 0.4 millimeters and its length may be between 1 and 2.5 meters depending on the length of the physical duct to be treated and the location of the athermoatic formation. The distal end 6B of the wire is preferably flattened on a length of between 0.6 and 0.8 meters.

Furthermore, so as to avoid any parasitic frequencies transversal to said wire, the frequency of the vibrations transmitted by the ultrasonic generator coincides with the actual resonance frequency of the wire.

Figure 6:
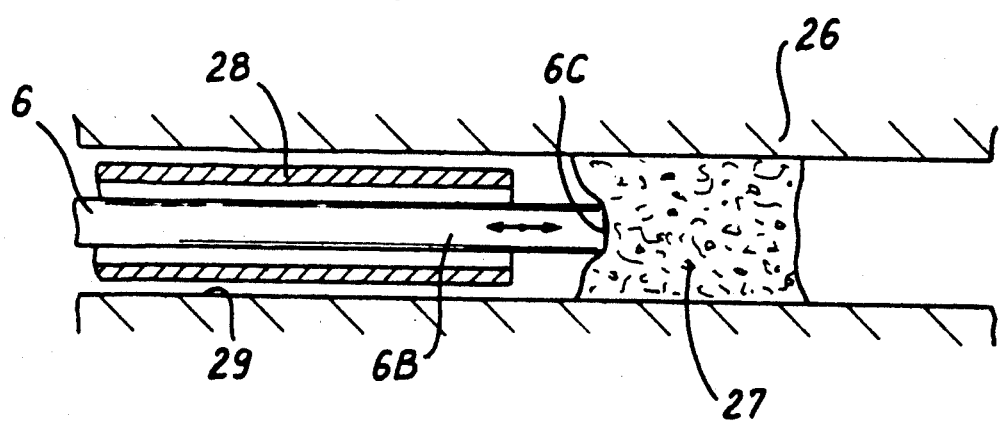
FIG. 6 is a diagrammatic sectional view of a physical duct, such as an artery, clogged up by an athermoa to be destroyed, this athermoa being acted against by the distal end of the wire.

FIG. 6 diagrammatically shows one section of an artery 26 clogged up by an athermoatic formation 27, for example.

So as to eliminate this formation, the practitioner firstly introduced a sheath 28 into the artery 26 until it is close to the athermoatic formation 27. This sheath 28 ensures the guiding of the wire 6 in the artery and protects the internal wall 29 of the artery 26 from any rubbings of the wire which might heat and harmfully burn the artery.

When the face 6C of the distal end 6B of the wire is roughly in contact with the athermoatic formation 27, the ultrasonic device 1 of the invention is actuated, the generated vibrations being optimally transmitted to the wire by means of the previously described linking means.

Figure 7A:
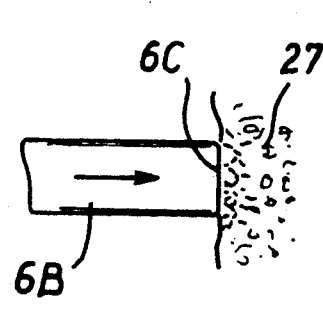
FIGS. 7a and 7b diagrammatically represent how the distal end of the wire acts against the atheroma to be destroyed.
Figure 7B:
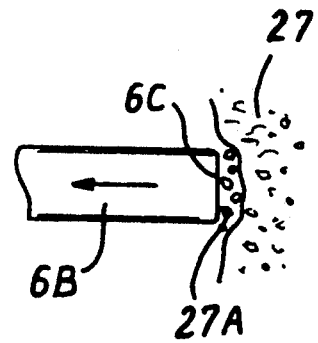

The longitudinally transmitted vibrations of the wire act against the athermoatic formation, as illustrated of FIGS. 7a and 7b, When the wire moves forward, the face 6C of the distal end 6B strikes the formation 27 so as to gradually provide the crumbling away and fragmentation of this formation. On the other hand, when the wire is moved backwards, the particles 27A of the athermoatic formation are gradually removed from the athermoa via partial vacuum and vaitation effects.

Furthermore, the practitioner may then remove the wire from the artery so as to introduce there a catheter whose distal end is provided with a deformable ballonet. Thus, by positioning the ballonet in the artery at the location of the formerly destroyed athermoatic formation, the practitioner is able to conventionally dilate the artery.

What is claimed is:

1. Ultrasonic percussion device comprising:
   an ultrasonic generator having a wall defining a hole having a conical section;
   a wire of millimetric diameter having a proximal end and a distal end;
   linking means connecting said proximal end of said wire to said generator, whereby said distal end is driven by percussive movement of said generator;
   wherein said linking means comprises:
   an elastically radially deformable sleeve receiving the proximal end of said wire, said sleeve being insertable in said hole and having a conical flared section which is complementary to the conical section of said hole; and,
   a clamping element threadly engaging said generator, rotation of said clamping element compressing said conical section of said sleeve against the complementary conical wall of said hole, thereby radially compressing said sleeve and clamping the proximal end of said wire within said sleeve.

2. Device according to claim 1, wherein said sleeve comprises a circular cylindrical section extended by said conical flared section, said cylindrical section being able to cooperate with the wall of said hole provided in generator, the conical flared section of said sleeve abutting against the complementary conical wall of said hole 3. Device according to claim 1, wherein radial slots are provided in at least the conical flared section of said sleeve for facilitating the radial deformation of the latter.

4. Device according to claim 4, wherein four radial slots are provided in said sleeve by being distributed equiangularly from one another.

5. Device according to claim 1, wherein said clamping element includes a threaded cylindrical lateral wall ended by an open bottom coming into contact with the end face of the flared section of said sleeve thus authorizing passage of said wire, whereas the end face of said cylindrical lateral wall of said clamping element opposite said open bottom abuts against the stop of said member.

6. Device according to claim 1, wherein the diameter of said wire is between 015 to 0.50 mm.

7. Device according to claim 6, wherein the diameter of said wire is roughly equal to 0.4 mm.

8. Device according to claim 1, wherein the distal end of said wire is flattened.

9. Device according to claim 8, wherein the distal end of said wire has an oblong section with one of its dimensions corresponding to the diameter of said wire, whereas the other dimension is smaller than the diameter of said wire.

10. Device according to claim 1, wherein said wire is made of a radio-opaque material.

* * * * *